United States Patent
Simonet et al.

(10) Patent No.: US 11,723,848 B2
(45) Date of Patent: Aug. 15, 2023

(54) OXIDIZING COMPOSITION FOR TREATING KERATIN FIBRES, COMPRISING A SCLEROGLUCAN GUM AND A PHOSPHORUS-BASED SEQUESTRANT

(71) Applicant: L'OREAL, Paris (FR)

(72) Inventors: Frédéric Simonet, Saint Ouen (FR); Koudedji Sow, Saint Ouen (FR); Aldo Pizzino, Clichy (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/471,604

(22) PCT Filed: Dec. 19, 2017

(86) PCT No.: PCT/EP2017/083607
§ 371 (c)(1),
(2) Date: Jun. 20, 2019

(87) PCT Pub. No.: WO2018/114987
PCT Pub. Date: Jun. 28, 2018

(65) Prior Publication Data
US 2020/0085708 A1 Mar. 19, 2020

(30) Foreign Application Priority Data
Dec. 20, 2016 (FR) ...................................... 1662864

(51) Int. Cl.
| | |
|---|---|
| *A61K 8/22* | (2006.01) |
| *A61K 8/24* | (2006.01) |
| *A61K 8/55* | (2006.01) |
| *A61K 8/73* | (2006.01) |
| *A61Q 5/04* | (2006.01) |
| *A61Q 5/08* | (2006.01) |
| *A61Q 5/10* | (2006.01) |
| *A61K 8/42* | (2006.01) |

(52) U.S. Cl.
CPC .................. *A61K 8/22* (2013.01); *A61K 8/24* (2013.01); *A61K 8/42* (2013.01); *A61K 8/55* (2013.01); *A61K 8/73* (2013.01); *A61Q 5/04* (2013.01); *A61Q 5/08* (2013.01); *A61Q 5/10* (2013.01); *A61K 2800/51* (2013.01)

(58) Field of Classification Search
None
See application file for complete search history.

(56) References Cited

U.S. PATENT DOCUMENTS

| | | | | |
|---|---|---|---|---|
| 2003/0078330 | A1* | 4/2003 | Legrand | A61K 8/22 524/306 |
| 2014/0326270 | A1* | 11/2014 | Degeorge | A45D 7/04 132/208 |
| 2016/0151263 | A1* | 6/2016 | Charrier | A61K 8/22 8/412 |

\* cited by examiner

*Primary Examiner* — Danah Al-Awadi
(74) *Attorney, Agent, or Firm* — Polsinelli PC

(57) ABSTRACT

The present invention relates to a cosmetic composition for treating keratin fibres, preferably human keratin fibres such as the hair, comprising, in a cosmetically acceptable medium: —one or more chemical oxidizing agents, —one or more scleroglucan gums, —one or more phosphorus-based sequestrants. The present invention also relates to a process for treating keratin fibres, preferably human keratin fibres such as the hair, comprising the application of the composition to the keratin fibres. The process according to the invention is preferably a process for bleaching, dyeing or permanently reshaping keratin fibres.

6 Claims, 1 Drawing Sheet

OXIDIZING COMPOSITION FOR TREATING KERATIN FIBRES, COMPRISING A SCLEROGLUCAN GUM AND A PHOSPHORUS-BASED SEQUESTRANT

CROSS REFERENCE TO RELATED APPLICATIONS

This application is a National Phase filing under 35 U.S.C. § 371 of PCT/EP2017/083607 filed on Dec. 19, 2017; which application in turn claims priority to Application No. 1662864 filed in France on Dec. 20, 2019. The entire contents of each application are hereby incorporated by reference.

The present invention relates to an oxidizing cosmetic composition for treating keratin fibres, preferably human keratin fibres such as the hair.

More precisely, the present invention relates to a cosmetic composition for treating keratin fibres, comprising at least one chemical oxidizing agent, at least one scleroglucan gum and at least one phosphorus-based sequestrant.

The present invention also relates to a process for treating keratin fibres, preferably human keratin fibres such as the hair, comprising the application of the composition to the fibres.

In cosmetics, oxidizing compositions are used in the fields of dyeing, bleaching and permanently reshaping keratin fibres, and in particular human keratin fibres such as the hair.

In the field of dyeing, oxidizing compositions may be used for oxidative dyeing.

The oxidizing compositions are mixed with oxidation dyes (bases and couplers), which are intrinsically colourless, to generate coloured and colouring compounds via a process of oxidative condensation.

Oxidizing compositions may also be used for direct dyeing. They are then used with direct dyes, which are coloured and colouring substances, to obtain colouring with a lightening effect on the hair.

In the field of bleaching, oxidizing compositions may be used alone applied to keratin fibres to bleach the hair. They may also be used in combination with compositions comprising peroxygenated salts such as persulfates when the oxidizing composition is based on hydrogen peroxide.

Permanently reshaping the hair consists, in a first step, in opening the —S—S— disulfide bonds of keratin (cystine) using a composition containing a suitable reducing agent (reduction step), and then, after having rinsed the head of hair thus treated, in reconstituting the disulfide bonds, in a second step, by applying to the hair, which has been placed under tension beforehand (curlers and others), an oxidizing composition (oxidation step, also known as the fixing step) so as finally to give the hair the desired shape. This technique thus makes it possible, without preference, either to make the hair wavy or to relax or uncurl it. The new shape given to the hair by a chemical treatment such as that above is eminently long-lasting and especially withstands the action of washing with water or shampoos, as opposed to the simple standard techniques of temporary reshaping, such as hairsetting.

Thickened or gelled compositions have many advantages.

Thus, they are generally easy to mix with other compositions, and easy to spread on the skin and/or the hair.

Furthermore, they do not run once they have been applied to the keratin fibres, which allows uniform application from the roots to the ends.

Finally, they have optimum safety of use since the risks of projection of the oxidizing agents, for example into the eyes or onto clothing, are reduced.

In parallel, translucent compositions have an aesthetic appearance that is particularly appealing to consumers.

However, the oxidizing compositions of the prior art are generally in the form of creams, which are opaque, or in the form of liquids.

The reason for this is that polymers which can thicken oxidizing compositions are rare, generally hydrolysed during storage due in particular to the very acidic pH of these compositions and to the presence of oxidizing agents.

Consequently, these thickened compositions have a tendency to degrade over time. The viscosity sometimes drops until the compositions become liquid.

Furthermore, the oxidizing agent content of these compositions is liable to drop during the period of storage.

Thus, there is a need to provide thickened, or even gelled, oxidizing compositions which are stable on storage and which conserve a constant content of oxidizing agents over time, in particular after long periods of storage.

Furthermore, compositions are also sought which have improved working qualities, in particular as regards the comfort of the scalp and the protection of keratin fibres.

Finally, cosmetic performance qualities that are improved relative to the oxidizing compositions conventionally used in the dyeing (oxidation dyeing or direct dyeing), bleaching or permanent reshaping of keratin fibres are sought.

In the field of dyeing and/or lightening the hair, oxidizing compositions which lead to good dyeing or lightening properties, especially in terms of power, chromaticity and selectivity in the case of dyeing, are also sought.

It has been found, surprisingly, that the combination of a natural polymer of the scleroglucan type and of a phosphorus-based sequestrant makes it possible to obtain an oxidizing composition that is stable over time, i.e. which in particular has a content of oxidizing agents and a viscosity that are constant over time, in particular after long periods of storage, with improved working qualities, leading to good cosmetic properties and to good dyeing and/or lightening properties in the case of dyeing/bleaching of the hair.

One subject of the present invention is thus a cosmetic composition for treating keratin fibres, preferably human keratin fibres such as the hair, comprising, in a cosmetically acceptable medium:

one or more chemical oxidizing agents,
one or more scleroglucan gums,
one or more phosphorus-based sequestrants.

The composition according to the invention has a thickened or even gelled texture and is translucent.

The composition according to the invention also has very good stability over time for several weeks. In particular, the oxidizing agent content of the composition varies little, or even not at all, over time.

For the purposes of the present invention, the term "stable" means that the following physical characteristics of the composition vary little, or even not at all, over time: content of oxidizing agents, appearance, pH, viscosity.

The composition according to the invention also has improved working qualities in particular as regards the comfort of the scalp and the protection of keratin fibres. Furthermore, it has the advantage of being easy to mix with other compositions, especially with one or more dyeing and/or bleaching compositions, and is easy to spread on keratin materials.

In addition, the composition according to the invention does not run once it has been applied to the keratin fibres, which allows uniform application from the roots to the ends.

The composition according to the invention also has optimum safety of use.

The composition according to the invention also has cosmetic performance qualities that are improved relative to the oxidizing compositions conventionally used in the dyeing (oxidation dyeing or direct dyeing), bleaching or permanent reshaping of keratin fibres.

Finally, in the field of dyeing and/or lightening the hair, the oxidizing composition according to the invention leads to good dyeing or lightening properties, especially in terms of power, chromaticity and selectivity in the case of dyeing.

A subject of the present invention is also a process for treating keratin fibres, preferably human keratin fibres such as the hair, comprising the application to the keratin fibres of the composition according to the invention.

The process according to the invention has the advantage of being simple to perform, in particular at room temperature.

Other characteristics and advantages of the invention will emerge more clearly on reading the description, the following examples and FIGS. 1a and 1b which show the change in viscosity over time of a comparative composition (FIG. 1a) and of a composition according to the invention (FIG. 1b).

In the text hereinbelow, and unless otherwise indicated, the limits of a range of values are included within that range, especially in the expressions "between" and "ranging from . . . to . . . ".

Moreover, the expression "at least one" used in the present description is equivalent to the expression "one or more".

The term "atmospheric pressure" means a pressure of 760 mmHg or $1.013 \times 10^5$ Pa.

The term "room temperature" means a temperature generally between 20 and 25° C., preferably 23° C.

According to the invention, the composition comprises one or more chemical oxidizing agents.

For the purposes of the present invention, the term "chemical oxidizing agent" means an oxidizing agent other than atmospheric oxygen.

Chemical oxidizing agents that may especially be mentioned include hydrogen peroxide, urea peroxide, alkali metal bromates or ferricyanides, peroxygenated salts, for instance persulfates, perborates, peracids and precursors thereof and percarbonates of alkali metals or of alkaline-earth metals such as sodium, potassium or magnesium.

One or more redox enzymes such as laccases, peroxidases and 2-electron oxidoreductases (such as uricase), optionally in the presence of the respective donor or cofactor thereof, may also be used as oxidizing agent.

Preferably, the chemical oxidizing agent(s) are chosen from hydrogen peroxide, urea peroxide, alkali metal bromates or ferricyanides, peroxygenated salts, and mixtures of these compounds.

Particularly preferably, the chemical oxidizing agent is hydrogen peroxide.

The chemical oxidizing agent(s) generally represent from 0.5% to 40% by weight, preferably from 1% to 30% by weight and more preferentially from 2% to 20% by weight relative to the total weight of the composition.

When the chemical oxidizing agent is hydrogen peroxide, it is generally in the form of an aqueous solution, the concentration of which may range, for example, from 5% to 60% by weight and especially from 20% to 50% by weight of hydrogen peroxide. However, the ranges indicated above are understood as weight of hydrogen peroxide and not as weight of aqueous solution.

According to the invention, the composition comprises one or more scleroglucan gums.

Scleroglucan gums are polysaccharides of microbial origin produced by a fungus of *Sclerotium* type, in particular *Sclerotium rolfsii*. They are polysaccharides constituted solely of glucose units.

Scleroglucan gums may or may not be modified. Preferably, the scleroglucan gums used in the present invention are unmodified.

Examples of scleroglucan gums that may be used in the present invention are, in a non-limiting manner, the products sold under the name Actigum CS, in particular Actigum CS 11 by the company Sanofi Bio Industries and under the name Amigum or Amigel by the company Alban Müller International.

Other scleroglucan gums, such as the gum treated with glyoxal described in French patent application No. 2 633 940, may also be used.

The scleroglucan gum(s) that may be used according to the invention generally represent at least 0.01% by weight, preferably from 0.01% to 20% by weight, more preferentially from 0.1% to 10% by weight and even more preferentially from 0.2% to 5% by weight relative to the total weight of the composition.

According to the invention, the composition comprises one or more phosphorus-based sequestrants.

The definition of a "sequestrant" (or "chelating agent") is well known to those skilled in the art and refers to a compound or a mixture of compounds that is (are) capable of forming a chelate with a metal ion. A chelate is an inorganic complex in which a compound (the sequestrant or chelating agent) is coordinated to a metal ion, i.e. it forms one or more bonds with the metal ion (formation of a ring including the metal ion).

A sequestrant (or chelating agent) generally comprises at least two electron-donating atoms which allow the formation of bonds with the metal ion.

In the context of the present invention, the sequestrant(s) are phosphorus-based sequestrants, i.e. sequestrants which comprise one or more phosphorus atoms, preferably at least two phosphorus atoms.

The phosphorus-based sequestrant(s) used in the composition according to the invention are preferentially chosen from:

inorganic phosphorus-based derivatives preferably chosen from phosphates and pyrophosphates of alkali metals or alkaline-earth metals, preferably of alkali metals, such as sodium pyrophosphate, potassium pyrophosphate, sodium pyrophosphate decahydrate; polyphosphates of alkali metals or alkaline-earth metals, preferably of alkali metals, such as sodium hexametaphosphate, sodium polyphosphate, sodium tripolyphosphate, sodium trimetaphosphate; which are optionally hydrated, and mixtures thereof organic phosphorus-based derivatives, such as organic (poly)phosphates and (poly)phosphonates, such as etidronic acid and/or alkali metal or alkaline-earth metal salts thereof, such as tetrasodium etidronate, and mixtures thereof.

Preferably, the phosphorus-based sequestrant(s) are chosen from linear or cyclic compounds comprising at least two phosphorus atoms bonded together covalently via at least one linker L comprising at least one oxygen atom and/or at least one carbon atom.

In one embodiment, the phosphorus-based sequestrant(s) are chosen from inorganic phosphorus derivatives preferably comprising at least two phosphorus atoms. More preferentially, the phosphorus-based sequestrant(s) are chosen from alkali metal or alkaline-earth metal pyrophosphates, better still from alkali metal pyrophosphates, in particular sodium pyrophosphate (also known as tetrasodium pyrophosphate).

In another embodiment, the phosphorus-based sequestrant(s) are chosen from organic phosphorus derivatives preferably comprising at least two phosphorus atoms. More preferentially, the phosphorus-based sequestrant(s) are chosen from etidronic acid (also known as 1-hydroxyethane-1, 1-diphosphonic acid) and/or alkali metal or alkaline-earth metal salts thereof, preferably alkali metal salts thereof such as tetrasodium etidronate.

Thus, preferably, the phosphorus-based sequestrant(s) are chosen from alkali metal pyrophosphates, etidronic acid and/or alkali metal salts thereof, and a mixture of these compounds.

Particularly preferably, the phosphorus-based sequestrant(s) are chosen from tetrasodium etidronate, etidronic acid, tetrasodium pyrophosphate, and a mixture of these compounds.

The phosphorus-based sequestrant(s) that may be used according to the invention generally represent at least 0.001% by weight, preferably from 0.001% to 5% by weight, more preferentially from 0.01% to 1% by weight and even more preferentially from 0.01% to 0.5% by weight relative to the total weight of the composition.

As indicated previously, the composition comprises a cosmetically acceptable medium.

The term "cosmetically acceptable medium" means a medium that is compatible with keratin fibres.

The composition according to the invention usually comprises water, which generally represents from 10% to 95% by weight, preferably from 20% to 95% by weight and preferably from 50% to 95% by weight, relative to the total weight of the composition.

The composition according to the invention may contain cosmetically acceptable organic solvents, more particularly including alcohols such as ethyl alcohol, isopropyl alcohol, benzyl alcohol and phenylethyl alcohol, or polyols or polyol ethers, for instance ethylene glycol monomethyl, monoethyl or monobutyl ether, propylene glycol or ethers thereof, for instance propylene glycol monomethyl ether, butylene glycol, dipropylene glycol, and also diethylene glycol alkyl ethers, for instance diethylene glycol monoethyl ether or monobutyl ether.

The solvents may then represent from 0.5% to 20% by weight and preferably from 2% to 10% by weight relative to the total weight of the composition according to the invention.

The composition according to the invention may also comprise one or more surfactants, more particularly nonionic, anionic, cationic, or amphoteric or zwitterionic surfactants.

The nonionic surfactant(s) that may be used according to the invention are described, for example, in the Handbook of Surfactants by M. R. Porter, published by Blackie & Son (Glasgow and London), 1991, pages 116-178. They are chosen especially from alcohols, α-diols and ($C_1$-$C_{20}$)alkylphenols, these compounds being polyethoxylated, polypropoxylated and/or polyglycerolated, and containing at least one fatty chain comprising, for example, from 8 to 18 carbon atoms, it being possible for the number of ethylene oxide and/or propylene oxide groups to especially range from 2 to 50, and for the number of glycerol groups to especially range from 2 to 30. Mention may also be made of copolymers of ethylene oxide and propylene oxide, polyoxyalkylenated fatty acid esters, alkylpolyglycosides which are optionally oxyalkylenated, alkyl glucoside esters, N-alkylglucamine and N-acyl-methylglucamine derivatives, aldobionamides and amine oxides.

Unless otherwise mentioned, for these surfactants the term "fatty compound" (for example a fatty acid) denotes a compound comprising, in its main chain, at least one saturated or unsaturated alkyl chain comprising at least 6 carbon atoms, preferably from 8 to 30 carbon atoms, and better still from 10 to 22 carbon atoms.

The term "anionic surfactant" means a surfactant comprising, as ionic or ionizable groups, only anionic groups. These anionic groups are preferably chosen from the groups $CO_2H$, $CO_2^-$, $SO_3H$, $SO_3^-$, $OSO_3H$, $OSO_3^-$, $O_2PO_2H$, $O_2PO_2H^-$ and $O_2PO_2^{2-}$.

The anionic surfactant(s) that may be used according to the invention are chosen especially from alkyl sulfates, alkyl ether sulfates, alkylamido ether sulfates, alkylaryl polyether sulfates, monoglyceride sulfates, alkylsulfonates, alkylamide sulfonates, alkylarylsulfonates, α-olefin sulfonates, paraffin sulfonates, alkylsulfosuccinates, alkyl ether sulfosuccinates, alkylamide sulfosuccinates, alkyl sulfoacetates, acylsarcosinates, acylglutamates, alkylsulfo succinamates, acylisethionates and N-acyltaurates, salts of alkyl monoesters and polyglycoside-polycarboxylic acids, acyllactylates, salts of D-galactoside uronic acids, salts of alkyl ether carboxylic acids, salts of alkyl aryl ether carboxylic acids, and salts of alkylamido ether carboxylic acids; or the non-salified forms of all of these compounds, the alkyl and acyl groups of all of these compounds containing from 6 to 24 carbon atoms and the aryl group denoting a phenyl group.

Some of these compounds may be oxyethylenated and then preferably comprise from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, they are not in the form of zinc salts, and they may be chosen from alkali metal salts, such as the sodium or potassium salt, and preferably the sodium salt, ammonium salts, amine salts, and in particular amino alcohol salts, and alkaline-earth metal salts such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

Use is preferably made of ($C_6$-$C_{24}$)alkyl sulfates, ($C_6$-$C_{24}$)alkyl ether sulfates, which are optionally oxyethylenated, comprising from 2 to 50 ethylene oxide units, and mixtures thereof, in particular in the form of alkali metal salts or alkaline-earth metal salts, ammonium salts or amino alcohol salts. More preferentially, the anionic surfactant(s) are chosen from ($C_{10}$-$C_{20}$)alkyl ether sulfates, and in particular sodium lauryl ether sulfate containing 2.2 mol of ethylene oxide.

The term "cationic surfactant" means a surfactant that is positively charged when it is contained in the composition according to the invention. This surfactant may bear one or more positive permanent charges or may contain one or more cationizable functions within the composition according to the invention.

The cationic surfactant(s) are preferably chosen from primary, secondary or tertiary fatty amines, which are optionally polyoxyalkylenated, or salts thereof, and quaternary ammonium salts, and mixtures thereof.

The fatty amines generally comprise at least one $C_8$-$C_{30}$ hydrocarbon-based chain.

Examples of quaternary ammonium salts that may especially be mentioned include:

those corresponding to general formula (I) below:

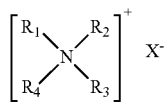
(I)

in which the groups $R_1$ to $R_4$, which may be identical or different, represent a linear or branched aliphatic group comprising from 1 to 30 carbon atoms, or an aromatic group such as aryl or alkylaryl, at least one of the groups $R_1$ to $R_4$ denoting a linear or branched aliphatic radical comprising from 8 to 30 carbon atoms, preferably from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups; $X^-$ is an anion chosen from the group of the halides, phosphates, acetates, lactates, ($C_1$-$C_4$)alkyl sulfates and ($C_1$-$C_4$)alkyl- or ($C_1$-$C_4$) alkylarylsulfonates.

Among the quaternary ammonium salts of formula (I), the ones that are preferred are, on the one hand, tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, the palmitylamidopropyltrimethylammonium salts, the stearamidopropyltrimethylammonium salts, the stearamidopropyldimethylcetearylammonium salts, or the stearamidopropyldimethyl(myristyl acetate)ammonium salts sold under the name Ceraphyl® 70 by the company Van Dyk. It is preferred in particular to use the chloride salts of these compounds;

quaternary ammonium salts of imidazoline, for instance those of formula (II) below:

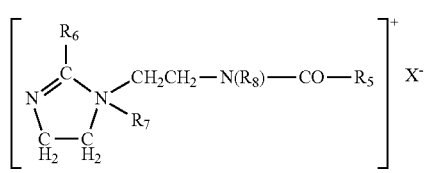
(II)

in which $R_5$ represents an alkenyl or alkyl group comprising from 8 to 30 carbon atoms, for example derived from tallow fatty acids, $R_6$ represents a hydrogen atom, a $C_1$-$C_4$ alkyl group or an alkenyl or alkyl group comprising from 8 to 30 carbon atoms, $R_7$ represents a $C_1$-$C_4$ alkyl group, $R_8$ represents a hydrogen atom or a $C_1$-$C_4$ alkyl group and $X^-$ is an anion chosen from the group of the halides, phosphates, acetates, lactates, alkyl sulfates, alkylsulfonates or alkylarylsulfonates, the alkyl and aryl groups of which preferably comprise, respectively, from 1 to 20 carbon atoms and from 6 to 30 carbon atoms. Preferably, $R_5$ and $R_6$ denote a mixture of alkenyl or alkyl groups comprising from 12 to 21 carbon atoms, for example derived from tallow fatty acids, $R_7$ denotes a methyl group and $R_8$ denotes a hydrogen atom. Such a product is sold, for example, under the name Rewoquat® W 75 by Rewo;

di- or triquaternary ammonium salts, in particular of formula (III):

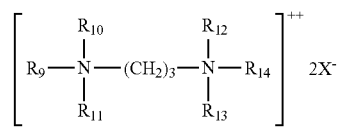
(III)

in which $R_9$ denotes an alkyl radical containing approximately from 16 to 30 carbon atoms, which is optionally hydroxylated and/or interrupted with one or more oxygen atoms, $R_{10}$ is chosen from hydrogen and an alkyl radical comprising from 1 to 4 carbon atoms or a group $(R_{9a})(R_{10a})(R_{11a})N-(CH_2)_3$, $R_{9a}$, $R_{10a}$, $R_{11a}$, $R_{11}$, $R_{12}$, $R_{13}$ and $R_{14}$, which may be identical or different, are chosen from hydrogen and an alkyl radical comprising from 1 to 4 carbon atoms, and $X^-$ is an anion chosen from the group of halides, acetates, phosphates, nitrates and methyl sulfates. Such compounds are, for example, Finquat CT-P, sold by the company Finetex (Quaternium 89), and Finquat CT, sold by the company Finetex (Quaternium 75);

quaternary ammonium salts containing at least one ester function, such as those of formula (IV) below:

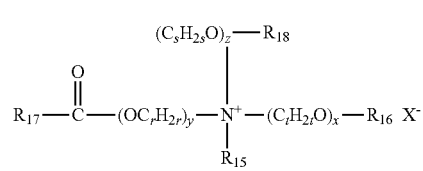
(IV)

in which:

$R_{15}$ is chosen from $C_1$-$C_6$ alkyl groups and $C_1$-$C_6$ hydroxyalkyl or dihydroxyalkyl groups;

$R_{16}$ is chosen from:

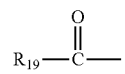

the group groups $R_{20}$, which are linear or branched, saturated or unsaturated $C_1$-$C_{22}$ hydrocarbon-based groups, a hydrogen atom, $R_{18}$ is chosen from:

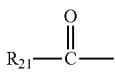

the group
groups $R_{22}$, which are linear or branched, saturated or unsaturated $C_1$-$C_6$ hydrocarbon-based groups,
a hydrogen atom,
$R_{17}$, $R_{19}$ and $R_{21}$, which may be identical or different, are chosen from linear or branched, saturated or unsaturated $C_7$-$C_{21}$ hydrocarbon-based groups;
r, s and t, which may be identical or different, are integers ranging from 2 to 6;
y is an integer ranging from 1 to 10;
x and z, which may be identical or different, are integers ranging from 0 to 10;
$X^-$ is a simple or complex and organic or mineral anion;
with the proviso that the sum x+y+z is from 1 to 15, that when x is 0 then $R_{16}$ denotes $R_{20}$, and that when z is 0 then $R_{18}$ denotes $R_{22}$.

The alkyl groups $R_{15}$ may be linear or branched, and more particularly linear.

Preferably, $R_{15}$ denotes a methyl, ethyl, hydroxyethyl or dihydroxypropyl group, and more particularly a methyl or ethyl group.

Advantageously, the sum x+y+z ranges from 1 to 10.

When $R_{16}$ is a hydrocarbon-based group $R_{20}$, it may be long and contain from 12 to 22 carbon atoms, or may be short and contain from 1 to 3 carbon atoms.

When $R_{18}$ is a hydrocarbon-based group $R_{22}$, it preferably contains 1 to 3 carbon atoms.

Advantageously, $R_{17}$, $R_{19}$ and $R_{21}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anion $X^-$ is preferably a halide (chloride, bromide or iodide) or an alkyl sulfate, more particularly methyl sulfate. However, use may be made of methanesulfonate, phosphate, nitrate, tosylate, an anion derived from an organic acid, such as acetate or lactate, or any other anion that is compatible with the ammonium bearing an ester function.

The anion $X^-$ is even more particularly chloride or methyl sulfate. Use is made more particularly, in the composition that may be used in the process according to the invention, of the ammonium salts of formula (IV) in which:
$R_{15}$ denotes a methyl or ethyl group,
x and y are equal to 1;
z is equal to 0 or 1;
r, s and t are equal to 2;
$R_{16}$ is chosen from:

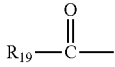

the group
methyl, ethyl or $C_{14}$-$C_{22}$ hydrocarbon-based groups,
a hydrogen atom;
$R_{18}$ is chosen from:

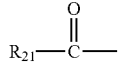

the group
a hydrogen atom;
$R_{17}$, $R_{19}$ and $R_{21}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

Advantageously, the hydrocarbon-based groups are linear.

Examples that may be mentioned include the compounds of formula (IV) such as the diacyl-oxy-ethyl-dimethyl-ammonium, diacyl-oxy-ethyl-hydroxy-ethyl-methyl-ammonium, monoacyl-oxy-ethyl-dihydroxy-ethyl-methyl-ammonium, triacyl-oxy-ethyl-methyl-ammonium and monoacyl-oxy-ethyl-hydroxy-ethyl-dimethyl-ammonium salts (chloride or methyl sulfate in particular), and mixtures thereof. The acyl groups preferably contain 14 to 18 carbon atoms and are obtained more particularly from a plant oil such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with $C_{10}$-$C_{30}$ fatty acids or with mixtures of $C_{10}$-$C_{30}$ fatty acids of plant or animal origin, or by transesterification of the methyl esters thereof. This esterification is followed by a quaternization using an alkylating agent such as an alkyl halide (preferably a methyl or ethyl halide), a dialkyl sulfate (preferably a methyl or ethyl sulfate), methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company CECA or Rewoquat® WE 18 by the company Rewo-Witco.

The composition according to the invention may contain, for example, a mixture of quaternary ammonium monoester, diester and triester salts with a weight majority of diester salts.

Use may also be made of the ammonium salts containing at least one ester function that are described in patents U.S. Pat. Nos. 4,874,554 and 4,137,180.

Use may be made of behenoylhydroxypropyltrimethyl-ammonium chloride sold by KAO under the name Quatarmin BTC 131.

Preferably, the ammonium salts comprising at least one ester function comprise two ester functions.

Among the quaternary ammonium salts containing at least one ester function, which may be used, it is preferred to use dipalmitoyl-ethyl-hydroxy-ethyl-methyl-ammonium salts.

The cationic surfactants are preferably chosen from those of formula (I) and those of formula (IV) and even more preferentially from those of formula (I).

The amphoteric or zwitterionic surfactant(s) that may be used according to the present invention may especially be secondary, tertiary or optionally quaternized aliphatic amine derivatives, in which the aliphatic group is a linear or branched chain containing from 8 to 22 carbon atoms, said amine derivatives containing at least one anionic group, for instance a carboxylate, sulfonate, sulfate, phosphate or phosphonate group. Mention may be made in particular of ($C_8$-$C_{20}$)alkylbetaines, sulfobetaines, ($C_8$-$C_{20}$)alkylamido ($C_3$-$C_8$)alkylbetaines or ($C_8$-$C_{20}$)alkylamido($C_6$-$C_8$)-alkylsulfobetaines.

Among the secondary, tertiary, or optionally quaternized aliphatic amine derivatives that may be used, as defined above, mention may also be made of the compounds of respective structures (B1) and (B2) below:

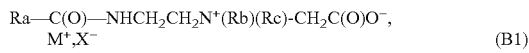
(B1)

in which formula (B1):

Ra represents a $C_{10}$-$C_{30}$ alkyl or alkenyl group derived from an acid RaCOOH preferably present in hydrolysed coconut oil, or a heptyl, nonyl or undecyl group;

Rb represents a beta-hydroxyethyl group; and

Rc represents a carboxymethyl group;

$M^+$ represents a cationic counterion derived from an alkali metal or alkaline-earth metal, such as sodium, an ammonium ion or an ion derived from an organic amine; and $X^-$ represents an organic or mineral anionic counterion, preferably chosen from halides, acetates, phosphates, nitrates, ($C_1$-$C_4$)alkyl sulfates, ($C_1$-$C_4$)alkyl or ($C_1$-$C_4$) alkylaryl sulfonates, in particular methyl sulfate and ethyl sulfate;

or alternatively $M^+$ and $X^-$ are absent;

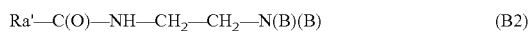
(B2)

in which formula:

B represents the group —$CH_2$—$CH_2$—O—X;

B' represents the group —($CH_2$)$_z$Y', with z=1 or 2;

X' represents the group —$CH_2$—C(O)OH, —$CH_2$—C(O) OZ', —$CH_2$—$CH_2$—C(O)OH, —$CH_2$—$CH_2$—C(O) OZ', or a hydrogen atom;

Y' represents the group —C(O)OH, —C(O)OZ', —$CH_2$—CH(OH)—$SO_3$H or the group —$CH_2$—CH (OH)—$SO_3$—Z;

Z' represents a cationic counterion resulting from an alkali metal or alkaline-earth metal, such as sodium, an ammonium ion or an ion resulting from an organic amine;

Ra' represents a $C_{10}$-$C_{30}$ alkyl or alkenyl group of an acid Ra'—COOH, which is preferably present in coconut oil or in hydrolysed linseed oil, or an alkyl group, especially a $C_{17}$ group and its iso form, or an unsaturated $C_{17}$ group.

The compounds of this type are classified in the CTFA dictionary, 5th edition, 1993, under the names disodium cocoamphodiacetate, disodium lauroamphodiacetate, disodium caprylamphodiacetate, disodium capryloamphodiacetate, disodium co coamphodipropionate, disodium lauroamphodipropionate, disodium caprylamphodipropionate, disodium capryloamphodipropionate, lauroamphodipropionic acid and cocoamphodipropionic acid.

By way of example, mention may be made of the cocoamphodiacetate sold by the company Rhodia under the trade name Miranol® $C_2$M Concentrate. Use may also be made of the compounds of formula (B'2):

Ra"—NH—CH(Y")—($CH_2$)$_n$—C(O)NH($CH_2$)$_{n'}$—N (Rd)(Re)   (B'2)

in which formula:

Y" represents the group —C(O)OH, —C(O)OZ", —$CH_2$—CH(OH)—$SO_3$H or the group —$CH_2$—CH (OH)—$SO_3$—Z";

Rd and Re, independently of each other, represent a $C_1$-$C_4$ alkyl or hydroxyalkyl radical;

Z" represents a cationic counterion derived from an alkali metal or alkaline-earth metal, such as sodium, an ammonium ion or an ion derived from an organic amine;

Ra" represents a $C_{10}$-$C_{30}$ alkyl or alkenyl group of an acid Ra"'—C(O)OH which is preferably present in coconut oil or in hydrolysed linseed oil;

n and n' denote, independently of each other, an integer ranging from 1 to 3.

Among the compounds of formula (B'2), mention may be made of the compound classified in the CTFA dictionary under the name sodium diethylaminopropyl cocoaspartamide and sold by the company Chimex under the name Chimexane HB.

Among the abovementioned amphoteric or zwitterionic surfactants, it is preferred to use ($C_8$-$C_{20}$ alkyl)betaines such as cocoylbetaine, ($C_8$-$C_{20}$ alkyl)amido($C_2$-$C_8$ alkyl)betaines such as cocoylamidopropylbetaine, and mixtures thereof.

More preferentially, the amphoteric or zwitterionic surfactant(s) are chosen from cocoylamidopropylbetaine and cocoylbetaine.

When they are present, the surfactant(s) preferably represent from 0.1% to 20% by weight and better still from 1% to 10% by weight relative to the total weight of the composition according to the invention.

The composition according to the invention may also comprise one or more silicones.

The silicones that may be used in accordance with the invention may be in the form of oils, waxes, resins or gums.

Preferably, the silicone(s) are chosen from polydialkylsiloxanes, in particular polydimethylsiloxanes (PDMSs), and organomodified polysiloxanes comprising at least one functional group chosen from amino groups, aryl groups and alkoxy groups.

Organopolysiloxanes are defined in greater detail in Walter Noll's Chemistry and Technology of Silicones (1968), Academic Press. They may be volatile or non-volatile.

The volatile silicones are more particularly chosen from silicones with a boiling point of between 60° C. and 260° C., and even more particularly silicones chosen from:

(i) cyclic polydialkylsiloxanes comprising from 3 to 7 and preferably from 4 to 5 silicon atoms. These are, for example, octamethylcyclotetrasiloxane sold especially under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide, of formula:

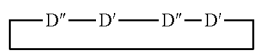

with D":

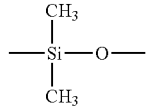

with D':

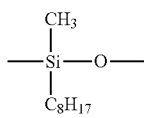

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold especially under the name SH 200 by the company Toray Silicone. Silicones belonging to this category are also described in the article published in Cosmetics and Toiletries, Vol. 91, January 76, pages 27-32—Todd & Byers Volatile Silicone Fluids for Cosmetics.

The non-volatile silicones that may be used according to the invention may preferably be non-volatile polydialkylsiloxanes, polydialkylsiloxane gums and resins, polyorganosiloxanes modified with organofunctional groups chosen from amine groups, aryl groups and alkoxy groups, and also mixtures thereof.

These silicones are more particularly chosen from polydialkylsiloxanes, among which mention may be made mainly of polydimethylsiloxanes bearing trimethylsilyl end groups. The viscosity of the silicones is measured at 25° C. according to ASTM Standard 445 Appendix C.

Among these polydialkylsiloxanes, mention may be made, in a non-limiting manner, of the following commercial products:
the Silbione® oils of the 47 and 70 047 series or the Mirasil® oils sold by Rhodia, for instance the oil 70 047 V 500 000;
the oils of the Mirasil® series sold by the company Rhodia;
the oils of the 200 series from the company Dow Corning, such as DC200 with a viscosity of 60 000 mm$^2$/s;
the Viscasil® oils from General Electric and certain oils of the SF series (SF 96, SF 18) from General Electric.

Mention may also be made of polydimethylsiloxanes bearing dimethylsilanol end groups, known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly(C$_1$-C$_{20}$)dialkylsiloxanes.

The silicone gums that may be used in accordance with the invention are especially polydialkylsiloxanes and preferably polydimethylsiloxanes with high number-average molecular masses ranging from 200 000 to 1 000 000, used alone or as a mixture in a solvent.

The solvent may be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products that may be used more particularly in accordance with the invention are mixtures such as:

mixtures formed from a polydimethylsiloxane with a hydroxy-terminated chain, or dimethiconol (CTFA), and from a cyclic polydimethylsiloxane, also known as cyclomethicone (CTFA), such as the product Q2 1401 sold by the company Dow Corning;
mixtures of a polydimethylsiloxane gum and a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;
mixtures of two PDMSs with different viscosities, and more particularly of a PDMS gum and a PDMS oil, such as the product SF 1236 from the company General Electric. The product SF 1236 is the mixture of a gum SE 30 defined above, with a viscosity of 20 m$^2$/s and of an oil SF 96 with a viscosity of $5 \times 10^{-6}$ m$^2$/s. This product preferably comprises 15% of gum SE 30 and 85% of an oil SF 96.

The organopolysiloxane resins that may be used in accordance with the invention are crosslinked siloxane systems containing the following units:

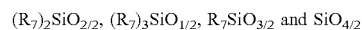

in which R$_7$ represents an alkyl containing 1 to 16 carbon atoms. Among these products, the ones that are particularly preferred are those in which R$_7$ denotes a C$_1$-C$_4$ lower alkyl group, more particularly methyl.

Among these resins, mention may be made of the product sold under the name Dow Corning 593 or those sold under the names Silicone Fluid SS 4230 and SS 4267 by General Electric, which are silicones of dimethyl/trimethylsiloxane structure.

Mention may also be made of the trimethyl siloxysilicate-type resins sold especially under the names X22-4914, X21-5034 and X21-5037 by Shin-Etsu.

The organomodified silicones that may be used in accordance with the invention are silicones as defined above and comprising in their structure one or more organofunctional groups attached via a hydrocarbon-based group.

The organomodified silicones may be polydiarylsiloxanes, especially polydiphenylsiloxanes, and polyalkylarylsiloxanes functionalized with the organofunctional groups mentioned previously.

The polyalkylarylsiloxanes are particularly chosen from linear and/or branched polydimethyl/methylphenylsiloxanes and polydimethyl/diphenylsiloxanes with a viscosity ranging from $1 \times 10^{-5}$ to $5 \times 10^{-2}$ m$^2$/s at 25° C.

Among these polyalkylarylsiloxanes, examples that may be mentioned include the products sold under the following names:
the Silbione® oils of the 70 641 series from Rhodia;
the oils of the Rhodorsil® 70 633 and 763 series from Rhodia;
the oil Dow Corning 556 Cosmetic Grade Fluid from Dow Corning;
the silicones of the PK series from Bayer, such as the product PK20;
the silicones of the PN and PH series from Bayer, such as the products PN1000 and PH1000;
certain oils of the SF series from General Electric, such as SF 1023, SF 1154, SF 1250 and SF 1265.

Among the organomodified silicones, mention may also be made of polyorganosiloxanes comprising:
substituted or unsubstituted amino groups, such as the products sold under the names GP 4 Silicone Fluid and GP 7100 by the company Genesee or the products sold under the names Q2 8220 and Dow Corning 929 or 939 by the company Dow Corning. The substituted amino groups are, in particular, $C_1$-$C_4$ aminoalkyl groups; alkoxylated groups, such as the product sold under the name Silicone Copolymer F-755 by SWS Silicones and Abil Wax® 2428, 2434 and 2440 by the company Goldschmidt.

When they are present, the silicones generally represent from 0.1% to 30% by weight and better still from 1% to 10% by weight relative to the total weight of the composition according to the invention.

The composition according to the invention may also comprise one or more non-silicone fatty substances.

The term "fatty substance" means an organic compound that is insoluble in water at ordinary room temperature (25° C.) and at atmospheric pressure (760 mmHg), with a solubility in water of less than 5%, preferably less than 1% and even more preferentially less than 0.1%.

In addition, the fatty substances are generally soluble in organic solvents under the same temperature and pressure conditions, for instance chloroform, ethanol, benzene, liquid petroleum jelly or decamethylcyclopentasiloxane.

The term "non-silicone fatty substance" means a fatty substance whose structure does not comprise any silicon atoms.

The non-silicone fatty substance(s) that may be used according to the invention are preferably chosen from hydrocarbons, fatty alcohols, fatty acid and/or fatty alcohol esters, non-salified fatty acids, and waxes, and mixtures thereof.

The fatty substance(s) may be liquid or non-liquid at room temperature and at atmospheric pressure.

The liquid fatty substances that may be used in the invention preferably have a viscosity of less than or equal to 2 Pa·s, better still less than or equal to 1 Pa·s and even better still less than or equal to 0.1 Pa·s at a temperature of 25° C. and at a shear rate of 1 $s^{-1}$.

The fatty substances generally have in their structure a hydrocarbon-based chain comprising at least 6 carbon atoms.

The term "liquid hydrocarbon" means a hydrocarbon composed solely of carbon and hydrogen atoms, which is liquid at ordinary temperature (25° C.) and at atmospheric pressure (760 mmHg, i.e. $1.013 \times 10^5$ Pa).

More particularly, the liquid hydrocarbons are chosen from:
  linear or branched, optionally cyclic, $C_6$-$C_{16}$ alkanes. Examples that may be mentioned include hexane, undecane, dodecane, tridecane, and isoparaffins, for instance isohexadecane, isododecane and isodecane;
  linear or branched hydrocarbons of mineral, animal or synthetic origin with more than 16 carbon atoms, such as liquid paraffins and derivatives thereof, petroleum jelly, liquid petroleum jelly, polydecenes, hydrogenated polyisobutene such as the product sold under the brand name Parleam® by the company NOF Corporation, and squalane.

Preferably, the liquid hydrocarbon(s) are chosen from liquid paraffins, isoparaffins, liquid petroleum jelly, undecane, tridecane and isododecane, and mixtures thereof.

In a most particularly preferred variant, the liquid hydrocarbon(s) are chosen from liquid petroleum jelly, isoparaffins, isododecane and a mixture of undecane and tridecane.

The term "liquid fatty alcohol" means a non-glycerolated and non-oxyalkylenated fatty alcohol, which is liquid at ordinary temperature (25° C.) and at atmospheric pressure (760 mmHg, i.e. $1.013 \times 10^5$ Pa). Preferably, the liquid fatty alcohols of the invention comprise from 8 to 30 carbon atoms and may be saturated or unsaturated.

The saturated liquid fatty alcohols are preferably branched. They may optionally comprise in their structure at least one aromatic or non-aromatic ring, which is preferably acyclic.

More particularly, the saturated liquid fatty alcohols of the invention are chosen from octyldodecanol, 2-decyltetradecanol, isostearyl alcohol and 2-hexyldecanol.

Octyldodecanol and 2-decyltetradecanol are most particularly preferred.

The unsaturated liquid fatty alcohols contain in their structure at least one double or triple bond, and preferably one or more double bonds. When several double bonds are present, there are preferably 2 or 3 of them, and they may be conjugated or unconjugated.

These unsaturated fatty alcohols may be linear or branched.

They may optionally comprise in their structure at least one aromatic or non-aromatic ring. They are preferably acyclic.

More particularly, the unsaturated liquid fatty alcohols that may be used in the invention are chosen from oleyl alcohol, linoleyl alcohol, linolenyl alcohol and undecylenyl alcohol.

Oleyl alcohol is most particularly preferred.

The term "liquid fatty ester" means an ester derived from a fatty acid and/or from a fatty alcohol, which is liquid at ordinary temperature (25° C.) and at atmospheric pressure (760 mmHg; i.e. $1.013 \times 10^5$ Pa).

More particularly, the liquid esters are chosen from esters of saturated or unsaturated, linear or branched $C_1$-$C_{26}$ aliphatic mono- or polyacids and from saturated or unsaturated, linear or branched $C_1$-$C_{26}$ aliphatic mono- or polyalcohols, the total number of carbon atoms in the esters being greater than or equal to 10.

Preferably, for the esters of monoalcohols, at least one from among the alcohol and the acid from which the esters of the invention are derived is branched.

Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isodecyl neopentanoate and isostearyl neopentanoate.

Esters of $C_4$-$C_{22}$ dicarboxylic or tricarboxylic acids and of $C_1$-$C_{22}$ alcohols and esters of monocarboxylic, dicarboxylic or tricarboxylic acids and of $C_4$-$C_{26}$ dihydroxy, trihydroxy, tetrahydroxy or pentahydroxy non-sugar alcohols may be used.

Mention may be made especially of diethyl sebacate, diisopropyl sebacate, diisopropyl adipate, di-n-propyl adipate, dioctyl adipate, diisostearyl adipate, dioctyl maleate, glyceryl undecylenate, octyldodecyl stearoyl stearate, pentaerythrityl monoricinoleate, pentaerythrityl tetraisononanoate, pentaerythrityl tetrapelargonate, pentaerythrityl tetraisostearate, pentaerythrityl tetraoctanoate, propylene glycol dicaprylate, propylene glycol dicaprate, tridecyl erucate, triisopropyl citrate, triisostearyl citrate, glyceryl trilactate, glyceryl trioctanoate, trioctyldodecyl citrate, trioleyl citrate, propylene glycol dioctanoate, neopentyl glycol diheptanoate, diethylene glycol diisononanoate and polyethylene glycol distearates.

Among the esters mentioned above, use is preferentially made of ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, propylene glycol dicaprylate, butyl stearate, isobutyl stearate; dioctyl malate, hexyl laurate, 2-hexyldecyl laurate, isononyl isononanoate or cetyl octanoate.

Among the liquid fatty esters, use may be made of sugar esters and diesters of $C_6$-$C_{30}$ and preferably $C_{12}$-$C_{22}$ fatty acids.

The term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Preferably, these said sugars are chosen from sucrose, glucose, galactose, ribose, fucose, maltose, fructose, mannose, arabinose, xylose and lactose, and derivatives thereof, especially alkyl derivatives, such as methyl derivatives, for instance methylglucose.

The sugar and fatty acid esters may be chosen especially from the group comprising the esters or mixtures of esters of sugars described previously and of linear or branched, saturated or unsaturated $C_6$-$C_{30}$ and preferably $C_{12}$-$C_{22}$ fatty acids.

If they are unsaturated, these compounds may comprise one to three conjugated or unconjugated carbon-carbon double bonds.

The esters according to this variant may also be chosen from mono-, di-, tri- and tetraesters, and polyesters, and mixtures thereof.

These esters may be, for example, oleates, laurates, palmitates, myristates, behenates, cocoates, stearates, linoleates, linolenates, caprates and arachidonates, and mixtures thereof, such as, especially, oleopalmitate, oleostearate or palmitostearate mixed esters.

More particularly, use is made of monoesters and diesters and especially of sucrose, glucose or methylglucose mono- or dioleates, stearates, behenates, oleopalmitates, linoleates, linolenates or oleostearates, or alternatively of methylglucose dioleate (Glucate® DO).

Among the sugar esters, use may be made of pentaerythrityl esters, preferably pentaerythrityl tetraisostearate, pentaerythrityl tetraoctanoate, and caprylic and capric acid hexaesters as a mixture with dipentaerythritol.

Among the natural or synthetic monoacid, diacid or triacid esters of glycerol, use may be made of plant oils or synthetic oils.

More particularly, said plant oil(s) or synthetic oil(s) are chosen from triglyceride oils of plant or synthetic origin, such as liquid fatty acid triglycerides containing from 6 to 30 carbon atoms, for instance heptanoic or octanoic acid triglycerides, or alternatively, for example, sesame oil, soybean oil, coffee oil, safflower oil, borage oil, sunflower oil, olive oil, apricot kernel oil, camellia oil, bambara pea oil, avocado oil, mango oil, rice bran oil, cotton seed oil, rose oil, kiwi seed oil, sea buckthorn pulp oil, blueberry seed oil, poppy seed oil, orange pip oil, sweet almond oil, palm oil, coconut oil, vernonia oil, marjoram oil, baobab oil, rapeseed oil, ximenia oil, pracaxi oil, caprylic/capric acid triglycerides such as those sold by the company Stéarineries Dubois or those sold under the names Miglyol® 810, 812 and 818 by the company Dynamit Nobel, jojoba oil and shea butter oil.

As liquid esters that may be used according to the invention, use is preferably made of triglycerides of plant origin, in particular oils chosen from avocado oil, olive oil, camellia oil and apricot kernel oil, and mixtures thereof, and $C_4$-$C_{22}$ dicarboxylic or tricarboxylic acid esters of $C_1$-$C_{22}$ alcohols, in particular 1,3-propanediol dicaprylate.

The term "fatty acid" means a non-salified fatty acid, i.e. the fatty acid must not be in the form of a generally soluble soap, i.e. it must not be salified with a base. More particularly, the liquid fatty acids that may be used according to the invention are chosen from the acids of formula RCOOH, in which R is a saturated or unsaturated, linear or branched radical preferably comprising from 7 to 39 carbon atoms.

Preferably, R is a $C_7$-$C_{29}$ alkyl or $C_7$-$C_{29}$ alkenyl group and better still a $C_{12}$-$C_{24}$ alkyl or $C_{12}$-$C_{24}$ alkenyl group. R may be substituted with one or more hydroxyl groups and/or one or more carboxyl groups.

Preferentially, the liquid fatty acid(s) are chosen from oleic acid, linoleic acid and isostearic acid.

The fatty substance(s) that may be used in the composition of the invention may also be chosen from fatty substances that are not liquid at room temperature (25° C.) and at atmospheric pressure (760 mmHg, i.e. $1.013\times10^5$ Pa).

The term "non-liquid fatty substance" preferably means a solid compound or a compound with a viscosity of greater than 2 Pa·s at a temperature of 25° C. and at a shear rate of $1\ s^{-1}$.

More particularly, the non-silicone "non-liquid" fatty substances are chosen from fatty alcohols, fatty acid and/or fatty alcohol esters, non-silicone waxes, fatty amines and fatty ethers, which are non-liquid and preferably solid.

More particularly, the non-liquid fatty alcohols that may be used according to the invention are chosen from linear or branched, saturated or unsaturated alcohols comprising from 8 to 30 carbon atoms.

Examples that may preferably be mentioned include cetyl alcohol, stearyl alcohol and a mixture thereof (cetylstearyl alcohol). Cetylstearyl alcohol is more particularly used.

The non-liquid esters of fatty acids and/or of fatty alcohols that may be used according to the invention are generally chosen from solid esters derived from $C_9$-$C_{26}$ fatty acids and from $C_9$-$C_{26}$ fatty alcohols.

Examples that may preferably be mentioned include octyldodecyl behenate, isocetyl behenate, cetyl lactate, stearyl octanoate, octyl octanoate, cetyl octanoate, decyl oleate, myristyl stearate, octyl palmitate, octyl pelargonate, octyl stearate, alkyl myristates such as cetyl myristate, myristyl myristate or stearyl myristate, and hexyl stearate.

The non-silicone wax(es) are chosen especially from carnauba wax, candelilla wax, esparto wax, paraffin wax, ozokerite, plant waxes, such as olive tree wax, rice wax, hydrogenated jojoba wax and absolute flower waxes, such as the blackcurrant blossom essential wax sold by Bertin (France), and animal waxes, such as beeswaxes or modified beeswaxes (cerabellina), and ceramides or analogues.

The ceramides or ceramide analogues, such as natural or synthetic glycoceramides, may be chosen from the compounds corresponding to formula (V) below:

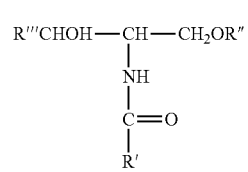

in which:
R' denotes a linear or branched, saturated or unsaturated alkyl radical derived from $C_{14}$-$C_{30}$ fatty acids, this radical possibly being substituted with a hydroxyl group in the alpha position, or a hydroxyl group in the omega position which is esterified with a saturated or unsaturated $C_{16}$-$C_{30}$ fatty acid;

R" denotes a hydrogen atom or a (glycosyl)n, (galactosyl)m or sulfogalactosyl radical, in which n is an integer ranging from 1 to 4 and m is an integer ranging from 1 to 8;

R'" denotes a $C_{15}$-$C_{26}$ hydrocarbon-based radical, saturated or unsaturated in the alpha position, this radical possibly being substituted with one or more $C_1$-$C_{14}$ alkyl radicals;

it being understood that, in the case of natural ceramides or glycoceramides, R'" may also denote a $C_{15}$-$C_{26}$ alpha-hydroxyalkyl radical, the hydroxyl group being optionally esterified with a $C_{16}$-$C_{30}$ alpha-hydroxy acid.

The ceramides that are preferred in the context of the present invention are those described by Downing in Arch. Dermatol, Vol. 123, 1381-1384, 1987, or those described in French patent FR 2 673 179.

The ceramide(s) that are more particularly preferred according to the invention are the compounds for which R' denotes a saturated or unsaturated alkyl derived from $C_{16}$-$C_{22}$ fatty acids, R" denotes a hydrogen atom and R'" denotes a linear, saturated $C_{15}$ radical.

Preferentially, the following compounds may especially be chosen: N-linoleoyldihydrosphingosine, N-oleoyldihydrosphingosine, N-palmitoyldihydrosphingosine, N-stearoyldihydrosphingosine, N-behenoyldihydrosphingosine, and a mixture of these compounds.

Even more preferentially, the ceramides used are those for which R' denotes a saturated or unsaturated alkyl radical derived from fatty acids, R" denotes a galactosyl or sulfogalactosyl radical and R'" denotes a —CH═CH—(CH$_2$)$_{12}$—CH$_3$ group.

Other waxes or waxy starting materials that may be used according to the invention are especially marine waxes such as those sold by Sophim under the reference M82, and waxes of polyethylene or of polyolefins in general.

The non-liquid fatty ethers that may be used according to the invention are chosen from dialkyl ethers and especially dicetyl ether and distearyl ether, alone or as a mixture.

Preferentially, the non-silicone fatty substance(s) that may be used according to the invention are chosen from hydrocarbons, in particular linear or branched $C_6$-$C_{16}$ alkanes and linear or branched hydrocarbons of mineral, animal or synthetic origin, of more than 16 carbon atoms, such as liquid paraffins and derivatives thereof, petroleum jelly, liquid petroleum jelly; fatty acid esters, in particular oils of plant origin and $C_4$-$C_{22}$ dicarboxylic or tricarboxylic acid esters of $C_1$-$C_{22}$ alcohols, these esters being chosen more preferentially from triglycerides of plant origin, and liquid fatty alcohols, and mixtures thereof.

When they are present, the fatty substance(s) generally represent from 1% to 50% by weight, preferably from 2% to 30% by weight and more preferentially from 5% to 15% by weight relative to the total weight of the composition of the invention.

The pH of the composition of the invention is generally between 1 and 7, preferably between 1 and 4 and more preferentially between 1.5 and 3.5.

The pH of the composition of the invention may be adjusted and/or stabilized by means of basifying agents and/or acidifying agents that are well known to those skilled in the art.

Basifying agents that may especially be mentioned include aqueous ammonia, alkali metal carbonates or bicarbonates, organic amines with a pKb at 25° C. of less than 12, in particular less than 10 and even more advantageously less than 6; among the salts of the amines mentioned previously with acids such as carbonic acid or hydrochloric acid, it should be noted that it is the pKb corresponding to the function of highest basicity.

Preferably, the amines are chosen from alkanolamines, in particular comprising a primary, secondary or tertiary amine function, and one or more linear or branched $C_1$-$C_8$ alkyl groups bearing one or more hydroxyl radicals; from oxyethylenated and/or oxypropylenated ethylenediamines, and from amino acids and compounds having the following formula:

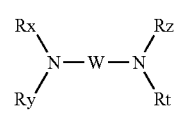

in which W is a $C_1$-$C_6$ alkylene residue optionally substituted with a hydroxyl group or a $C_1$-$C_6$ alkyl radical; Rx, Ry, Rz and Rt, which may be identical or different, represent a hydrogen atom or a $C_1$-$C_6$ alkyl, $C_1$-$C_6$ hydroxyalkyl or $C_1$-$C_6$ aminoalkyl radical.

Acidifying agents that may especially be mentioned include hydrochloric acid, (ortho)phosphoric acid, sulfuric acid, boric acid, and also carboxylic acids, for instance acetic acid, lactic acid or citric acid, or sulfonic acids.

The composition according to the invention may also contain additives such as natural or synthetic, anionic, amphoteric or zwitterionic, nonionic or cationic, associative or non-associative polymeric thickeners other than scleroglucan gum, non-polymeric thickeners such as electrolytes, styling polymers, sugars, nacreous agents, opacifiers, sunscreens, vitamins or provitamins, fragrances, organic or mineral particles, and preserving agents.

A person skilled in the art will take care to select the optional additives and the amount thereof such that they do not harm the properties of the composition of the present invention.

These additives may be present in the composition according to the invention in an amount ranging from 0 to 50% by weight, relative to the total weight of the composition.

The composition according to the invention may also comprise one or more dyes chosen from oxidation dyes and/or direct dyes.

However, preferably according to the invention, the composition does not comprise any dye.

The composition according to the invention is advantageously in the form of a transparent to translucent, thickened or even gelled fluid.

The composition according to the invention has a viscosity preferably ranging from 1 to 100 Pa·s, more preferentially from 1 to 10 Pa·s, at a shear rate of 10 s$^{-1}$, the viscosity being measured at 25° C. and atmospheric pressure with a ThermoHaake RS600 rheometer equipped with a titanium C60/1° geometry (0.055 mm gap).

The composition according to the invention may be prepared via any means known to those skilled in the art.

Another subject of the present invention relates to a process for treating keratin fibres, preferably human keratin fibres such as the hair, comprising the application to the keratin fibres of the composition as defined above.

In a first embodiment of the process according to the invention, it concerns a process for bleaching keratin fibres.

In this embodiment, the oxidizing composition according to the invention is applied to the keratin fibres, optionally with a preliminary step of mixing with at least one other composition, said other composition possibly comprising one or more peroxygenated salts, preferably chosen from persulfates.

In a second embodiment of the process according to the invention, it concerns a process for dyeing keratin fibres.

Thus, in this second embodiment, the process according to the invention comprises the application of the composition as defined previously, simultaneously or sequentially, with a dye composition comprising one or more oxidation dyes and/or one or more direct dyes.

The dye composition used in this dyeing process may comprise:

- one or more standard oxidation dye precursors chosen especially from oxidation bases such as phenylenediamines, bis(phenyl)alkylenediamines, para-aminophenols, ortho-aminophenols and heterocyclic bases, and the addition salts thereof, optionally combined with one or more common couplers, for instance meta-phenylenediamines, meta-aminophenols, meta-diphenols, naphthalene-based couplers and heterocyclic couplers, and also the addition salts thereof, and/or
- one or more direct dyes chosen, for example, from synthetic or natural, cationic, anionic or nonionic direct dyes.

Examples of particularly suitable direct dyes that may be mentioned include nitrobenzene dyes; azo direct dyes; azomethine direct dyes; methine direct dyes; azacarbocyanines, for instance tetraazacarbocyanines (tetraazapentamethines); quinone and in particular anthraquinone, naphthoquinone or benzoquinone direct dyes; azine direct dyes; xanthene direct dyes; triarylmethane direct dyes; indoamine direct dyes; indigoid direct dyes; phthalocyanine direct dyes, porphyrin direct dyes and natural direct dyes, alone or as mixtures. In particular, mention may be made of direct dyes from among: azo; methine; carbonyl; azine; nitro (hetero) aryl; tri(hetero)arylmethane; porphyrin; phthalocyanine and natural direct dyes, alone or as mixtures.

The dye composition usually comprises dyes (oxidation dyes and/or direct dyes) in a content ranging, for example, from 0.0001% to 10% by weight, and preferably from 0.005% to 5% by weight, relative to the weight of the dye composition.

The dye composition may also comprise other ingredients such as fatty substances, chosen especially from those listed previously.

The dye composition may also contain various adjuvants such as, in a non-limiting manner, nonionic, cationic, anionic or amphoteric surfactants, and especially those mentioned previously in the context of the oxidizing composition according to the invention; anionic, nonionic or amphoteric polymers or mixtures thereof; antioxidants; penetrants; sequestrants; fragrances; dispersants; film-forming agents; ceramides; preserving agents; opacifiers.

The above adjuvants may be present in an amount, for each of them, of between 0.01% and 20% by weight, relative to the weight of the dye composition.

The dye composition may also comprise water and/or one or more organic solvents such as those mentioned above.

When they are present, the organic solvents generally represent between 1% and 40% by weight and preferably between 5% and 30% by weight relative to the total weight of the dye composition.

The dye composition is preferably aqueous.

The pH of the dye composition generally ranges from 6 to 11, preferentially from 8.5 to 11.

It may be adjusted by addition of acidifying agents and/or basifying agents such as those mentioned previously.

Preferably, according to the second embodiment, the dyeing process according to the invention is performed by applying to the keratin fibres the composition according to the invention in the presence of the abovementioned dye composition. These two compositions may be applied one after the other, without intermediate rinsing, or alternatively mixed just before application to the keratin fibres.

The process according to the invention may be repeated several times so as to obtain the desired colouring.

In a third embodiment of the process according to the invention, it concerns a process for permanently reshaping keratin fibres.

According to this third embodiment, the process according to the invention generally comprises a first step of applying a reducing composition comprising one or more reducing agents, followed by a step of applying the composition according to the invention.

According to this third embodiment, the process according to the invention may advantageously comprise a step of placing the keratin fibres under tension (for example with rollers) and/or a step of heat treatment of the keratin fibres.

Irrespective of the embodiment of the process according to the invention, the composition(s) described previously, optionally mixed beforehand, are applied to wet or dry keratin fibres.

The composition(s) are usually left in place on the fibres for a time generally ranging from 1 minute to 1 hour and preferably from 5 minutes to 30 minutes.

The temperature during the process is conventionally between 20 and 80° C., preferably between 20 and 60° C.

On conclusion of the treatment, the keratin fibres are advantageously rinsed with water. They may optionally be washed with a shampoo, followed by rinsing with water, before being dried or left to dry.

The examples that follow serve to illustrate the invention without, however, being limiting in nature.

EXAMPLES

Example 1

Preparation of the Compositions

Compositions A and B are prepared with the ingredients and in the contents as indicated in Table I below.

Composition A is comparative and comprises xanthan gum. Composition B is according to the invention and comprises scleroglucan gum.

The amounts are indicated as grams of active material, unless otherwise indicated.

TABLE I

| Ingredients | A (comp.) | B (inv.) |
|---|---|---|
| Xanthan gum | 1.5 | — |
| Scleroglucan gum | — | 1.5 |
| Tetrasodium etidronate | 0.06 | 0.06 |
| Tetrasodium pyrophosphate | 0.04 | 0.04 |
| Sodium salicylate | 0.035 | 0.035 |
| Hydrogen peroxide | 4.5 | 4.5 |
| Phosphoric acid | qs pH = 2.2 ± 0.2 | qs pH = 2.2 ± 0.2 |
| Deionized water | qs 100 | qs 100 |

T0 for the characterizations of the compositions (cf. below) corresponds to the state of the system 24 hours after adjusting the pH.

Characterizations of the Compositions

The viscosity is measured in the following manner (at atmospheric pressure):

ThermoHaake RS600 rheometer equipped with a titanium C60/1° geometry (0.055 mm gap)

flow at 25° C. in stages at a shear rate of 10 s$^{-1}$ the viscosity of the compositions is measured each week.

Results

FIG. 2a shows the change in viscosity of composition B at room temperature (B1) and at 45° C. (B2) as a function of time (indicated in weeks).

Figure 1A:
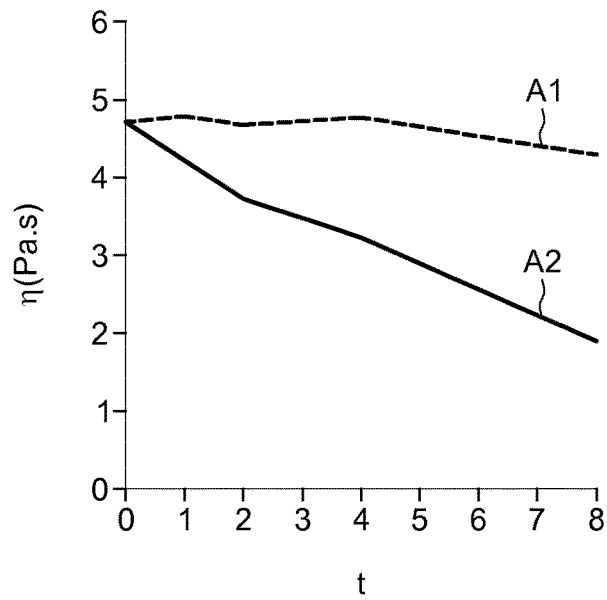
FIG. 1a shows the change in viscosity of composition A at room temperature (A1) and at 45° C. (A2) as a function of time (indicated in weeks).
Figure 1B:
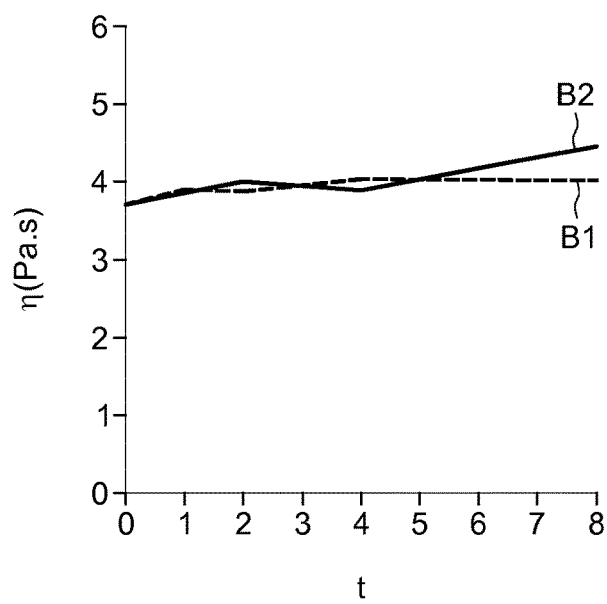

It is found that composition B according to the invention which comprises scleroglucan gum has a viscosity which varies very little over time, both at room temperature and at 45° C., unlike comparative composition A whose viscosity varies more substantially, especially at 45° C.

Composition B according to the invention is thus more stable than comparative composition A which comprises xanthan gum.

Example 2

Preparation of the Compositions

Compositions C and D are prepared with the ingredients and in the contents as indicated in Table II below.

Composition C is comparative and comprises a non-phosphorus-based sequestrant. Composition D is according to the invention and comprises a phosphorus-based sequestrant.

The amounts are indicated as grams of active material, unless otherwise indicated.

TABLE II

| Ingredients | C (comp.) | D (inv.) |
| --- | --- | --- |
| Scleroglucan gum | 1.5 | 1.5 |
| Hydrogen peroxide | 12 | 12 |
| Tetrasodium salt of EDTA | 0.06 | — |
| Tetrasodium etidronate | — | 0.06 |
| Phosphoric acid | qs pH = 2.0 ± 0.2 | qs pH = 2.0 ± 0.2 |
| Deionized water | qs 100 | qs 100 |

Characterizations of the Compositions

Macroscopic Characterization

Once compositions C and D were prepared, they were stored, either at room temperature or at 45° C.

On the day after preparation, comparative composition C shows bubbles, in a markedly larger number than in composition D according to the invention, manifestly on account of the decomposition of hydrogen peroxide (release of oxygen), this taking place at both storage temperatures.

Viscosity Measurement

The viscosity is measured in the following manner:

ThermoHaake RS600 rheometer equipped with a titanium C60/1° geometry (0.055 mm gap)

flow at 25° C. in stages at the following shear rates and times: 1 s$^{-1}$ (10 min), 10 s$^{-1}$ (5 min), 100 s$^{-1}$ (2 min) and 1000 s$^{-1}$ (30 s).

The viscosity recorded at a given flow rate is that which corresponds to the first stabilized flow rate at less than 1% of the nominal value (for example 1.01) and at equilibrium.

T0 for the characterizations of the compositions (cf. below) corresponds to the state of the system 24 hours after adjusting the pH.

The compositions are stored at 45° C. and the viscosity is measured at T0, at one day (T1), one week (T2) and two weeks (T3).

The viscosity values are given in Tables III and IV below.

TABLE III

Composition C (comparative)

| Shear rate (s$^{-1}$) | Viscosity (in Pa · s) | | | |
| --- | --- | --- | --- | --- |
|  | T0 | T1 | T2 | T3 |
| 1 | 27.3 | 28.2 | 13.0 | 0.008 |
| 10 | 3.61 | 3.70 | 2.42 | 0.006 |
| 100 | 0.46 | 0.46 | 0.36 | 0.0055 |
| 1000 | 0.075 | 0.070 | 0.054 | 0.0050 |

TABLE IV

Composition D (invention)

| Shear rate (s$^{-1}$) | Viscosity (in Pa · s) | | | |
| --- | --- | --- | --- | --- |
|  | T0 | T1 | T2 | T3 |
| 1 | 25.7 | 29.3 | 29.1 | 25.4 |
| 10 | 3.36 | 3.78 | 3.97 | 3.73 |
| 100 | 0.42 | 0.47 | 0.49 | 0.48 |
| 1000 | 0.069 | 0.073 | 0.073 | 0.066 |

It is found that composition D according to the invention has a low variation in viscosity over time, irrespective of the shear rate, unlike comparative composition C.

Composition D according to the invention is stable over time. On the other hand, comparative composition C is unstable and becomes entirely liquid after a few weeks.

The invention claimed is:

1. A cosmetic composition for treating keratin fibres comprising, in a cosmetically acceptable medium:
   hydrogen peroxide representing from 2% to 20% by weight relative to the total weight of the composition,
   one or more scleroglucan gums representing from 0.2% to 5% by weight relative to the total weight of the composition,
   one or more phosphorus sequestrants comprising one or more phosphorus atoms chosen from tetrasodium pyrophosphate, etidronic acid, tetrasodium etidronate and mixtures thereof representing from 0.01% to 0.5% by weight relative to the total weight of the composition, and
wherein the composition does not comprise any oxidation dye or any direct dye.

2. The composition according to claim 1, wherein the pH of the composition ranges from 1 to 7.

3. A process for treating keratin fibres comprising the application to the keratin fibres of the composition as claimed in claim 1.

4. The process according to claim 3, characterized in that it is a process for bleaching keratin fibres.

5. The process according to claim 3, characterized in that it is a process for permanently reshaping keratin fibres.

6. The composition according to claim 1 which is an oxidizing composition.

* * * * *